(12) United States Patent
Malmquist

(10) Patent No.: US 6,783,993 B1
(45) Date of Patent: Aug. 31, 2004

(54) HOMOGENIZING OF SMALL-VOLUME MIXTURES BY CENTRIFUGATION AND HEATING

(75) Inventor: Mats Malmquist, Uppsala (SE)

(73) Assignee: Alphahelix AB, Uppsala (SE)

( * ) Notice: Subject to any disclaimer, the term of this patent is extended or adjusted under 35 U.S.C. 154(b) by 0 days.

(21) Appl. No.: 09/937,383

(22) PCT Filed: Mar. 24, 2000

(86) PCT No.: PCT/SE00/00586

§ 371 (c)(1),
(2), (4) Date: Sep. 25, 2001

(87) PCT Pub. No.: WO00/58013

PCT Pub. Date: Oct. 5, 2000

(30) Foreign Application Priority Data

Mar. 25, 1999 (SE) .................................. 9901104
Jun. 22, 1999 (SE) .................................. 9902378

(51) Int. Cl.[7] .................................................. G01N 1/10
(52) U.S. Cl. .......................... 436/177; 422/72; 422/99; 435/91.2; 435/287.2; 435/273.3; 435/303.1; 494/13; 494/14
(58) Field of Search ................ 435/6, 91.2, 287.2, 435/287.3, 288.7, 303.1; 422/72, 99, 102, 104, 101; 436/177; 494/13, 14

(56) References Cited

U.S. PATENT DOCUMENTS 3,600,900 A  8/1971  Buddecke
3,856,470 A  12/1974  Cullis et al.
4,498,896 A  2/1985  Leis
5,232,667 A  * 8/1993  Hieb et al. ............... 422/82.04
5,772,572 A  6/1998  Koch et al.

FOREIGN PATENT DOCUMENTS

| DE | 195 01 105 | 7/1996 |
| EP | 0 073 512 | 3/1983 |
| EP | 0 160 282 | 11/1985 |
| EP | 0 169 306 | 1/1986 |
| EP | 0 693 560 | 1/1996 |
| GB | 2 235 639 | 3/1991 |
| WO | WO 97/43230 | 11/1997 |
| WO | WO 98/49340 | 11/1998 |

* cited by examiner

*Primary Examiner*—William H. Beisner
(74) *Attorney, Agent, or Firm*—Young & Thompson

(57) ABSTRACT

The efficient temperation of a sample is achieved when the sample is subjected to centrifugation simultaneously wish heating and optionally also cooling. This is achieved in a device comprising at least a rotor (1) for holding reaction vessels (2), a motor (3), connected to the rotor, a processor (4) for controlling the speed of the rotor, and elements (5 and 6) for heating and cooling the contents of the reaction vessels, wherein the elements (6) for heating cover the apices of the reaction vessels for at least part of the rotational path of the vessels and that the elements for heating operate at a temperature significantly higher than the meeting temperature of the reaction vessels. The invention further relates to a method for performing chemical reactions and in particular a method for performing biochemical reactions involving thermocycling, for example PCR-reactions.

26 Claims, 3 Drawing Sheets

HOMOGENIZING OF SMALL-VOLUME MIXTURES BY CENTRIFUGATION AND HEATING

The present invention relates to the field of chemical reactions requiting temperation and/or incubation of the reaction mixture and in particular chemical reactions in liquid media The present invention discloses a new device and method for efficient and homogenous mixing, temperation and/or incubation of reaction mixtures.

BACKGROUND OF THE INVENTION

Many important industrial processes as well as procedures applied in laboratories of various kids are dependent on chemical reactions. Commonly the time consumed for completing a process or procedure is determined by the time it takes for some specific chemical reaction or reactions to reach equilibrium. This is often referred to as the kinetic properties of a chemical reaction or simply reaction kinetics. A host of variables influence the reaction kinetics in each case, for instance the concentrations of reactants, temperature, presence of catalytic agents etc.

Typically, increased temperature makes chemical reactions faster by speeding up key mechanisms like bringing molecules or molecule domains in contact with each other. Therefore it is common to heat the reaction vessels, for example bringing them in contact with an open flame, hot gas, hot liquid, hot sand or a solid material. This procedure is often referred to as incubation.

One typical problem involved with incubations of fluid reaction mixtures is thermal heterogeneity, because the parts of the reaction mixture being in close contact with the walls of the reaction vessel will become heated before the more central parts of the reaction mixture. In many cases there is a risk of part of the reaction mixture becoming overheated before other parts even reach the desired temperature. This leads to temperature gradients forming in the reaction mixture. Hot subsets of the reaction mixture has normally lower density than cold subsets which tend to generate temperature gradients or discrete layers of more or less isothermal bodies of liquid, so called thermoclines. Thus warm, less dense portions of the reaction mixture tend to find a position above cold, denser portions. Molecular motion and currents in the reaction mixture will eventually homogenize the reaction mixture with respect to temperature, a process referred to as temperation of the reaction mixture. The time it takes to temperate a reaction mixture may contribute substantially to the time required for the complete reaction.

However, time-consumption in itself is not the sole problem involved with temperation of chemical reaction mixtures. In certain incubation procedures such as the repetitive temperations involved in so called thermocycling processes, e.g. for performing polymerase chain reactions, also known as PCR-reactions, long temperation periods also leads to unwanted side-reactions, sometimes causing severe quality problems with respect to the accuracy and specificity of the obtained PCR-product.

In the ongoing strive to miniaturize chemical reaction volumes, as evident e.g. in the field of high throughput screening, several other problems are encountered. In a small reaction vessel, such as a well on a microtitre plate, both the mixing and temperation of sample and reagents may become severely restricted. When two or more miscible fluids are mixed, we normally assume that they first form a homogenous mixture, which then reacts. This is however rarely the case.

Conventional microtitre plates and cuvettes are often manufactured from polystyrene, a hydrophilic polymer. Without dwelling on the exact behaviour of the liquid at the vessel boundaries, it can be concluded that stagnant areas will form and insufficient mixing easily occur in a small reaction vessel, such as a well on a microtitre plate. The properties of the reactants and sample fluids also influence their interaction with each other and with the vessel boundaries. Partial segregation, the formation of layers, aggregation and so on are only a few examples of irregularities that can be encountered in a reaction vessel.

There are reasons for distinguishing between two different processes causing problems with heterogeneous temperature distribution in a reaction mixture. The process caused by the lower fluidity close to the walls of a reaction vessel is a problem increasing when reaction scale decreases. In contrast, the problem involved with central parts of the liquid body being colder than the liquid close to walls when heating a reaction vessel, increases when reaction scale increases. This is the reason why thermocycling devices for processes in which proper temperation is required (e.g. processes like PCR) have a very narrow dynamic range with respect to the reaction scale. Typically, in PCR-reactions these problems are most severe when reaction volumes are less than 5 $\mu$L and larger than 50 $\mu$L.

Another problem, seemingly unrelated to the mixing and temperation issues, is that of evaporation. In order to avoid evaporation, there exists a tendency to make the reaction vessels and in particular the wells on microtitre plates deeper and more narrow. Naturally, this further enhances the previously mentioned problems of insufficient mixing and temperation.

So far, temperature heterogeneity has been discussed in terms of properties in a single reaction vessel. Especially when discussing miniaturisation of assays yet another dimension of temperation heterogeneity need to be considered; that of variation between reaction vessels. In assays with comparative purposes (i.e. with or without quantitative analysis like screening for novel drug candidates, mutations in nucleic acids, single nucleotide polymorphism and so forth) it is important to consider the reproducibility, commonly referred to as well-to-well uniformity.

Since the processes leading to poor thermal uniformity are difficult to predict quantitatively, the only available solution to the problem is often to focus on means to enhance the homogenisation processes. To do this, various strategies are applied.

One is to use reaction vessels with specific flat or oblong configurations in order to minimize the distance between the central and peripheral parts of the bulk of the reaction mixture. An example of this is to perform the incubation in thin capillaries as described by Wittwer, C. T. et al. (The LightCycler™: A Microvolume Multisample Fluorimeter with Rapid Temperature Control, *Bio Techniques* 22:176–181, January 1997). One disadvantage with this approach is that the glass capillaries, loosely attached to their plastic holding portions, require extensive manual handling. The choice of glass capillaries makes possible both rapid temperation of the reaction mixture and detection of fluorescence after amplification. However, a glass capillary tends to maximize the surface-to-fluid contact, with all the consequences this has on mixing and temperation. Further, the use of glass capillaries has the additional drawback of obstructing the post-PCR processing of the sample. Examples of post-PCR processing include DNA sequencing procedures etc.

Other ways to solve the problem with mixing and temperature heterogeneity is to introduce perturbation by agitating or shaking the reaction vessel. Specific instruments designed for this purpose are for example various kinds of flask shakers and so called Vortex machines. A problem often encountered with this approach is that the perturbation periodicity may cause currents or standing waves and therefore incomplete homogeneity.

Another approach for homogeisation is the use of ultrasonic waves in a standard procedure called sonication. The latter procedure is, unfortunately, often difficult to combine with a number of standard incubation methods.

Yet another approach is the use of flow-through systems, where a constantly mowing liquid is subjected to heating.

Within the field of PCR, much attention has been given to heat transfer and to the question of faster ramping, i.e. how to shorten the speed for temperature adjustments in both the heating and cooling phase.

Closest Prior Art

WO 98/49340 (PCT/AU98/00277) discloses a temperature cycling device and method where a reaction mixture and a sample is loaded into loading wells on a disposable rotor, which rotor is then placed into a centrifugal thermal cycling device and spun, so that the reaction mixture and sample are moved by centrifugal force to a reaction well at the periphery of the rotor. The device comprises heating means, for example infrared lights, convection heating elements or microwave sources. Interestingly, also provisions for cooling the rotor are included in the specification. According to one embodiment, the rotor speed is increased, resulting in air being drawn into the device and rapidly cooling the contents of the reaction chambers at the periphery of the rotor. In addition to ambient air, a coolant gas can be used. Refrigerated air is given as an example of coolant gases. Importantly, the disclosure of WO 98/49340 implies the use of different speeds of rotation. Further, WO 98/49340 does not address the problems of mixing and homogenous temptation For example, it does not specify the direction of heating, nor does it contemplate simultaneous heating and cooling.

DE 19501105 A1 discloses a centrifuge with a temperature control system where a circulating fluid enters the rotor from above and flows out-wards and down-wards in the direction of the radius, around the test-tubes or sample containers. The inventor of the centrifuge according to DE 19501105 criticises the hitherto known devices using a radiating source of heat and rejects them as unsatisfactory.

It was the purpose of the present invention to solve the problem with time consuming and insufficient mixing and temperation steps in procedures where incubation of small-volume chemical reaction mixtures are involved by finding means for effective mixing and homogenisation. Importantly, said means should be compatible with means for unhindered analysis of the reaction and preferably also applicable in existing and future technologies in the fields of chemical and biotechnological reactions, screening and analysis, such as high throughput screening, amplification reactions etc.

In particular, the need for a fast and accurate thermocycling device and corresponding method is nor yet satisfied by the prior art devices and methods.

SUMMARY OF THE INVENTION

This problem is solved by the invention according to the characterising portion of the attached claims, which are hereby incorporated. The invention comprises both devices and methods as disclosed in the description an defined in the attached claims. Further problems solved by the invention and advantages obtained can be derived from the description and drawings.

SHORT DESCRIPTION OF THE FIGURES

The present invention is described below with reference to the attached drawings in which FIG. 1 shows schematically a first embodiment of the invention, having a device for temperature measurement (7) communicating with a processor (4);

DESCRIPTION

Figure 1:
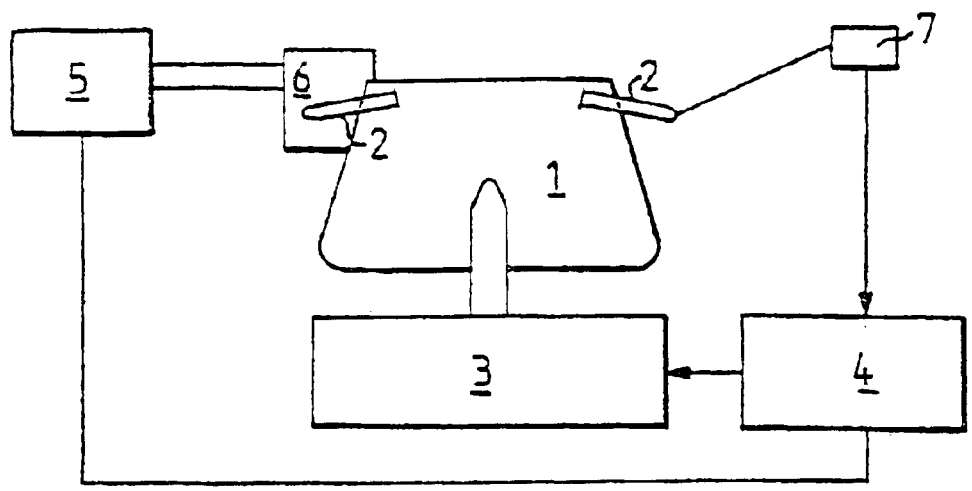

In the following description of the invention, certain definitions will be used. They are to be interpreted as outlined below:

The direction of the gravitational field: Described with vectors, the direction of the gravitation field is the same as the resulting vector when a vector representing the centrifugal force, that is a vector at right angle to the axis of the centrifuge rotor directed from the centre of the rotor, is added to the vector representing the gravitation of earth. Consequently, downwards is in the present text defined as the same direction as the gravitation field as defined by the summed vectors representing centrifugal force and gravitation.

Reaction mixture: Any fluid reaction mixture preferably a liquid reaction mixture, in which the reaction kinetics are influenced by temperature and where a faster, more efficient and homogenous temperation is desired. Examples of reactions, suitable for the present device and method are chemical/biochemical reactions within the field of high throughput screening and biochemical reactions involving repeated temperation, e.g. cyclic temperature changes, including a polymerase chain reaction (PCR), a ligase chain reaction (LCR), a "gapped-LCR-reaction", a nucleic acid sequence-based amplification (NASBA), a self-sustained replication (3SR), a transcription mediated amplification (TMA), a stand displacement amplification (SDA), a target amplification, a signal amplification, or a combination of any of the above.

Typically a polymerase chain reaction involves the following steps:

1) Preparation of the reaction mixtures, i.e. preparation of the samples to be test
2) Amplification, i.e. the exponential replication of the DNA molecules; and 3) Detection of specific sequences for example by electrophoresis or hybridisation Step 2) involves repeated temperature changes to take the reaction mixture through the steps of annealing and extension of the nucleotide stands. Inefficient temperation, that is diffuse temperatures in the reaction mixture leads to unspecific amplification products. The necessity of a fast and homogenous temperation of the reaction mixture is central for the quality and reliability of the reaction.

Reaction vessel: Any vessel capable of containing a reaction mixture within the temperature range necessary for performing the reaction. Examples of reaction vessels suitable is for use according to the invention include, but are not limited to, the following: test tubes, so called micro tubes, Eppendorf-tubes, a single well or a multitude of wells in a microtitre plate, such as a microtitre plate of the 96-hole format, and various formats with a high density arrays of wells, such as the 192-hole format, the 384-hole format, denser formats or the like. The reaction vessel for use according to the present invention can be a conventional, commercially obtainable reaction vessel as listed above, or a reaction vessel specially adapted for use in the inventive device, for example including an optical element at its distal end, a special colour or surface for absorbing heat at its distal end or having opaque, isolating or reflective surfaces on its side walls etc.

The reaction mixture is situated in a reaction vessel, e.g. a vessel having at least one opening and one closed end, substantially in the opposite direction of the open end. Said vessel is loaded with a sample and at least one reactant, which by definition constitute the reaction mixture and which mixture is to be homogeneously incubate. Reactants are dispensed through the open end which after dispensing may be sealed, for example using a lid. Dispensing of reagents may be performed using manual or automated pipetting devices or, in a preferred embodiment of the invention, using predispensed reagent capillaries (PCT/SE91/00343) or reagent cartridges (PCT/SE97/01562).

The closed end is defined as the distal end pointing in the same direction as the current gravitation field. The open end or the end closed with a lid or reagent cartridge, is called the proximal end. Thus, when no centrifugation occur, the distal end of a reaction vessel is often directed downwards in accordance of the gravitation field of the earth. In congruence with this statement, upwards in the present text is defined as the direction in opposition to the gravitation field that affects the reaction vessel with content in a specific situation. The proximal end is consequently directed upwards or in a direction opposite to the centrifugal force.

A device according to the present invention is shown in FIG. 1 comprising means, such as a rotor 1 for holding at least one reaction vessel 2 with contents; means for subjecting the said at least one reaction vessel and its contents to a centrifugal force, such as a motor 3; means 5 and 6 for heating the part of the reaction vessel directed outwards in relation to the centrifugal force; and means for cooling the proximal end of the reaction vessel (not shown). A temperature sensor 7 is shown, with a line indicating schematically, that the reading is taken from the sample containing end of a rotating reaction vessel 2. The temperature sensor 7 is preferably an IR sensor.

Using an IR sensor or other rapid sensor, an on-line measurement of temperature is achieved. The fist and accurate temperature measurement makes it possible to use the very high temperatures described.

In FIG. 1, a processor 4 is shown. This processor can be any conventional logic circuit loaded with operating instructions in the form of computer code, or a circuit specially adapted for the inventive device. The functions of the processor include at least the following: to process the temperature signal from the temperature sensor 7 and to control the operation of the motor 3 and the heating/cooling source 5 according to one or more programmes, chosen by the operator.

Preferably said means 1 for holding at least one reaction vessel is a rotor, e.g. a rotor chosen among the following: a drum rotor, a swing-bucket rotor and a fixed angle rotor. Further, the chosen rotor is preferably modified to allow unhindered thermal contact between the distal or "lower" end of the reaction vessels and the heating source. Likewise, the rotor may suitably modified to allow efficient cooling of the proximal end.

The heating source 5 and 6 can be any heating source, capable of heating the distal ends of the reaction vessels, e.g. a radiating source, such as a heating element with electric resistance wires, an IR-source, a microwave element and the like. According to one embodiment of the present invention, the heating and cooling is effected through the use of at least one external source of heat and cold (illustrated throughout the figures as 5) connected to a mantle 6. The mantle embraces the rotational path of the reaction vessels 2 during at least part of this path as indicated in the cross sections of FIGS. 1, 2, 3 and 4.

Figure 5:
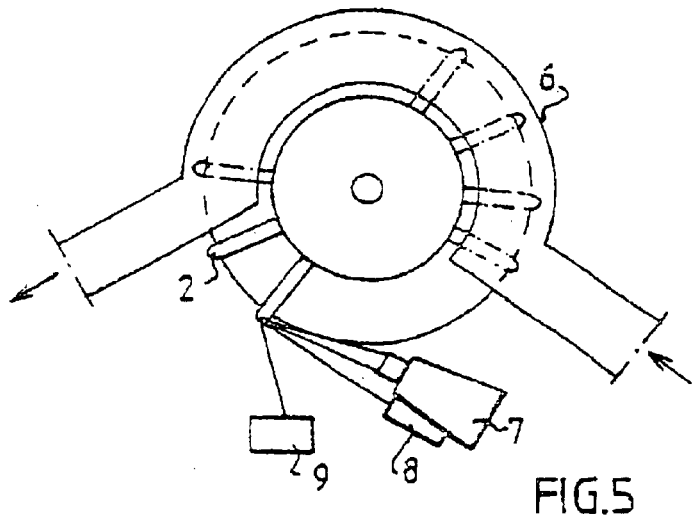
FIG. 5 shows a schematic view from above of an embodiment according to FIG. 2.
Figure 6:
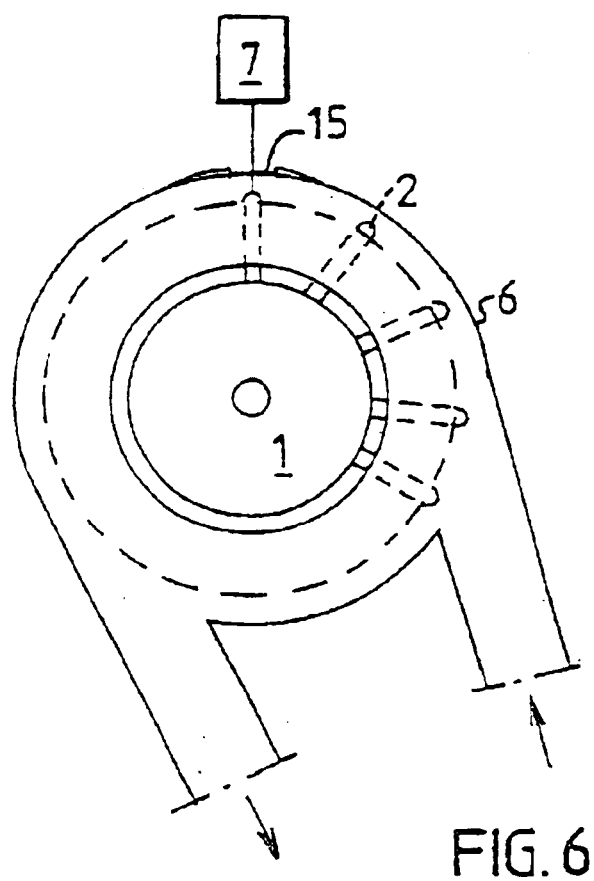
FIG. 6 shows a schematic view from above of an embodiment, e.g. an embodiment according to FIG. 1.
Figure 7:
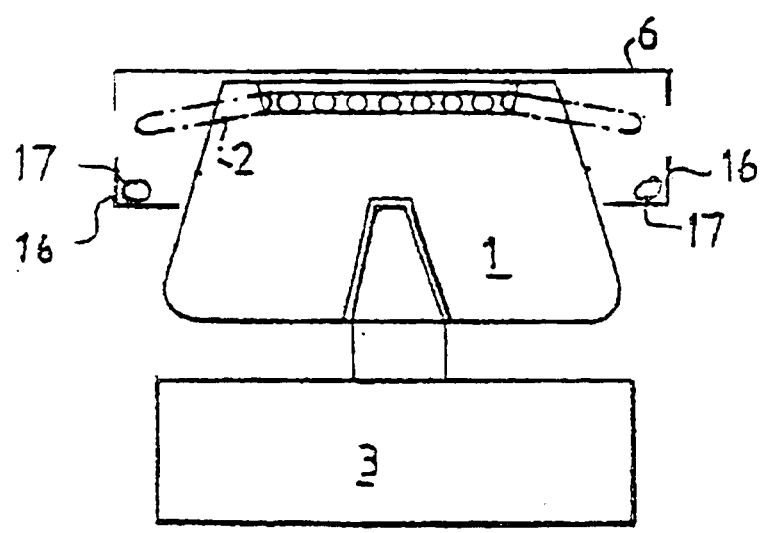
FIG. 7 shows a schematic cross section of a device with a heat source (17) placed in a lower mantle half (16) which can be moved vertically.

Preferably, the mantle 6 is adapted to the shape of the rotor, as schematically indicated in FIGS. 5 and 6, showing two embodiments of the invention. In FIG. 7 an embodiment is shown, where the mantle or a part thereof is movable in relation to the rotational path of the reaction vessels. The movable part of the mantle is then preferably a circular or partially circular reflector 16 containing a source of heat 17 and arranged so that it can be moved closer to and away from the rotational part of the reaction vessels.

The heating source may also be situated inside the rotor, at the distal or lower ends of the reaction vessels (not shown). According to one embodiment of the invention, a telecentric lens is positioned between the hearing source and the reaction vessel or reaction vessels.

The cooling source or means for cooling can be chosen among convection cooling and a circulating cooling medium, e.g. a refrigerated gas, such as air and preferably nitrogen. In an embodiment, such as those shown in the attached drawings, the cooling medium is let into the mantle and thus comes in contact with the rotating reaction vessels. According to another embodiment (not shown) the environment of the rotor is refrigerated with exception of the mantle. By moving the mantle in relation to the rotor, e.g. raising or lowering it into close proximity of the rotting reaction vessels, said vessels are heated. By lowering, raising or otherwise removing the mantle, the surrounding cold environment is again allowed to contact the rotating reaction vessels. Instead of moving the mantle, the rotor can be moved while the mantle is kept at a fixed position.

The reaction vessels 2 can be any one of the following a set of individual tubes, e g. Eppendorf-tubes, individual wells on a microtitre plate or individual test tubes.

Figure 2:
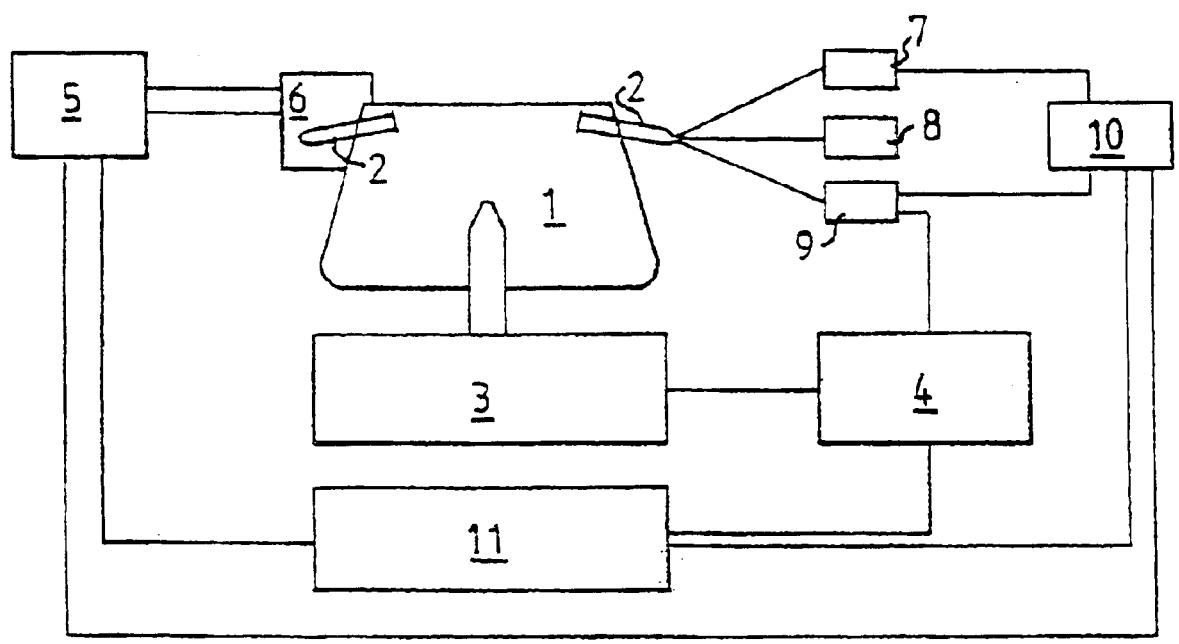
FIG. 2 shows a second embodiment of the invention, where the device for temperature measurement (7) is supplemented with a laser source (8) and sensor (9)

FIG. 2 shows schematically an embodiment where a radiation source 8 emits radiation, e.g. a laser beam which intersects the rotational path of the reaction vessels. The reflectance of this radiation is detected by a sensor 9. The temperature sensor 7, e.g. an IR sensor, may communicate with the reflectance sensor 9 via a processor 10, e.g. for the purpose of adjusting the temperature measurements to the rotational speed. The radiation source 8 and the reflectance sensor 9 may also be used for detecting chemical reactions in the samples, e.g. the light reflectance or emission indicating the end point of a reaction or a positive or negative test answer.

Further in FIG. 2 a user interface 11 is indicated. Said user interface can include a key board or similar for inputting the selection of operating parameters or choice of pre-programmed operating schemes, a display for showing the progress of the operation, process parameters etc.

According to a preferred embodiment, the device according to the invention includes means for reading information regarding sample identity, operating instructions etc. Examples of such information includes operating parameters, such as time and temperature, number of cycles, post-PCR temperature etc., sample information, such as date, source, patient identity, quality etc. and reagent information, such as batch number, date, reagent quantity, type etc.

According to one embodiment, the samples or reaction vessels carry the above or similar information, e.g. in the form of optically readable signs, such as bar codes, optically readable discs etc, or electronically readable information, such as information contained on a magnetic carrier or on an integrated circuit or chin. Using this embodiment, a high degree of safety and control is achieved. Operator error is minimized. The samples are identified and the operation performed according to information contained in each sample carrier, e.g. each microtitre plate The information can be read by the operator, e.g. using a barcode reader, or by the device, automatically detecting the information when the samples are loaded into the device.

Figure 3:
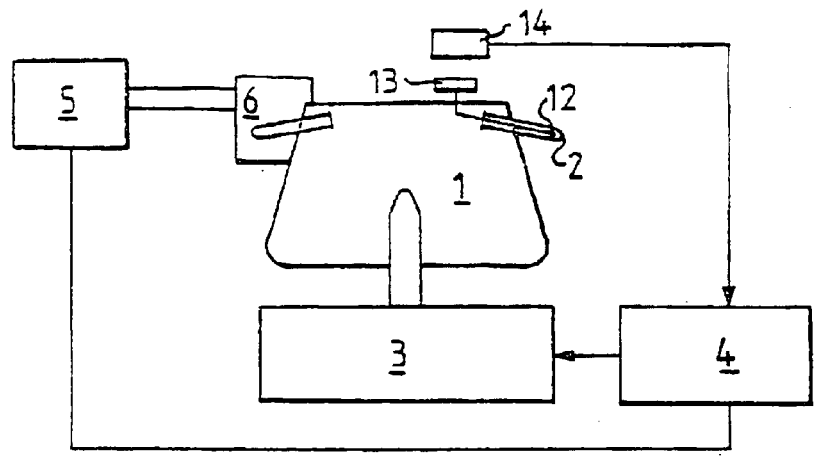
FIG. 3 shows a third embodiment of the invention, where the temperature is measured by a probe (12), communicating via a transmitter (13) and receiver (14) with the processor (4)

In FIG. 3 is shown an embodiment, where temperature reading and control is effected via a sensor 12 placed in one of the reaction vessels, communicating with the processor 4 via a transmitter 13 and receiver 14. The sensor is e.g. a thermocouple and the transmitter/receiver system can be a system utilising IR signals.

Figure 4:
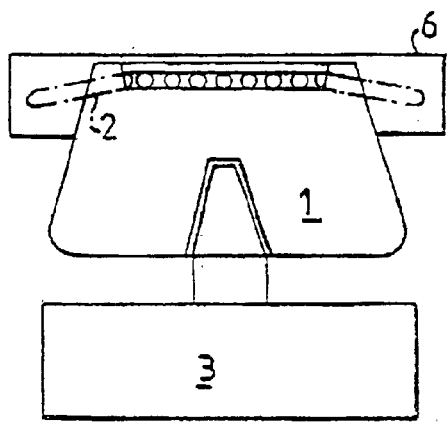
FIG. 4 shows a schematic cross section of a device according to the invention, showing basic components, such as the heating mantle (6)

FIG. 4 shows a schematic cross section of a device according to the invention, where the mantle 6 is shown. The reaction vessels 2, the rotor 1 and the motor 3 are as disclosed above.

FIG. 5 shows a schematic view from above, e.g. of an embodiment according to FIG. 2. The mantle 6 having an inlet and an outlet, indicated by arrows, leading into and out from the mantle, respectively. It is seen, that the mantle covers only part of the rotational path of the reaction vessels 2, leaving a sector for unhindered measurement. Here the measurement is shown including the IR sensor 7, a laser source 8 and a reflectance sensor 9.

In FIG. 6 an embodiment is shown, where the mantle 6 surrounds the entire rotational path of the reaction vessels 2. The measurements, here indicated by the sensor 7, are taken through the mantel, preferably through a section 15 of the mantle, being permeable to or able to transmit the signals detected by the sensor.

FIG. 7 shows a schematic cross section of an embodiment where the heating source 17, e.g. a tubular IR lamp, is arranged in a movable reflector 16. By activating the IR lamp and raising the reflector into close proximity of the rotating reaction vessels, the sample volumes are efficiently heated. When the lamps are deactivated and the reflector lowered, the heat dissipates quickly from said sample volumes. The cooling can be aided by refrigerating the entire inner volume of the device or the volume closes to the rotating reaction vessels. The reflector 16 need not be arranged below the rotational path of the reaction vessels, but can also be arranged above or around said pat. In those cases, the reflector is moved downwards or inwards it comes in close proximity of the rotating reaction vessels.

According to one embodiment of the invention, said device is capable of subjecting the contents of the reaction vessel or vessels to significant centrifugal force, preferably a centrifugal force in the internal of about 500×g to about 20.000×g or higher, preferably in the interval of about 1.500×g to about 20.000×g and most preferably about 5.000×g to about 15.000×g. The temperation achieved by the present inventive device or method is naturally a function of the reaction volume, its constitution, the temperature and the centrifugal force.

Further, a device according to one embodiment of the invention comprises means for cooling the part of the reaction vessel directed inwards in relation to the centrifugal force. In this case, the rotor is modified to allow unhindered thermal contact between the proximal or "upper" end of the reaction vessels and the cooling medium.

The means for heating comprise at least one source of heat, for instance a radiation source emitting radiation within a wavelength range generating heat, e.g. an IR source, an electric element hot gas or hot liquid, which is positioned within or connected to a centrifuge in such way that the heat when emitted, reach the distal end or ends, of one or several reaction vessels when these reaction vessels, being appropriately situated in the rotor of the centrifuge, are centrifuged. When the invention is intended for cyclic heating and cooling, this source of heat can be switched on and off without terminating the centrifugation. The effect of the heat source should be high enough to bring the complete amount of reaction mixture contained in the reaction vessel or reaction vessels, to the temperature being appropriate for the desired chemical reaction The heating means can preferably comprise a temperature sensor or sensors or a thermostat for monitoring and controlling the heating.

According to a one embodiment of the invention, hot air is forced into a space surrounding the rotating reaction vessels or at least the apices of said vessels. This space is referred to as a "heating mantle".

The hot air referred to in this context is air or a suitable gas mixture, heated to a temperature which exceeds the melting temperature of the material of the reaction vessels, e.g. the thermoplastic of the Eppendorf-tubes or microtitre wells. The temperature is preferably as high as possible, given the restrictions posed by the equipment used, and preferably a temperature in the interval of 200 to 800 degrees Celsius, most preferably about 600 degrees Celsius.

The cooling effect is achieved at unchanged rotational speed. According to one embodiment of the invention, the heating mantle is removed from the immediate vicinity of the reaction vessels, either by moving the heating mantle in relation to the rotor, e.g. by raising the heating mantle, or by lowering the rotor. The rapidly rotating reaction vessels will then come in contact with surrounding air or gas mixture, e.g. the air inside the centrifuge or air aspirated from the surrounding room. According to a preferred embodiment, the air or gas mixture inside the centrifuge is cooled to a temperature below the ambient temperature. The rotor can also be enclosed in a larger space, which is refrigerated. When the heating mantle is moved away from immediate contact with the reaction vessels, the refrigerated air will rapidly cool the vessels.

The means for cooling can comprise means for leading a cooling medium, e.g. a gas, liquid or ambient air into close proximity of the proximal or "upper" end of the reaction vessel. A suitable cooling medium is liquid nitrogen or refrigerated nitrogen gas.

When the invention is used, reaction vessels including the complete reaction mixture or a subset of this, are placed in the rotor of the centrifuge with the closed end directed downwards or otherwise according to standard practice for centrifuging the reaction vessels in question. The centrifuge is then started, that is, the engine which brings the rotor to spin is switched on. When the rotor has accelerated to the chosen gravitation force, the rotation is kept at constant speed. The heating source is now switched on leading to increased temperature predominantly at the apices of the reaction vessels. The heat will be transferred through the material of the walls of the reaction vessels, to the most distal part of the bulk of the reaction mixture. Increased molecular motion due to increased temperature will expand, that is, decrease the density of this heated part of the reaction mixture. Due to the pressure caused by the gravitation field acting on more dense subsets of the reaction mixture, the parts with lower density will be forced to move upwards, immediately replaced by reaction mixture with higher density. This dense part will then be heated by means of the same process of heat transfer from the heating source. The density of this part of the reaction mixture will decrease and move upwards and become replaced by cooler reaction mixture. The means for cooling, according to one embodiment of the invention, acting simultaneously on the upper or proximal part of the reaction vessel will cooperate to ensure thorough mixing and homogenization. This chain of events will carry on, eventually leading to a thoroughly mixed, homogenous reaction mixture and a homogeneous temperature distribution in the bulk of the reaction mixture.

According to a preferred embodiment, the device according to the invention is equipped with an IR-sensor, and preferably a focussed IR-sensor monitoring the temperature of the contents in the rotating vessels. Prior art methods of temperature control often use a thermocouple, placed in one reaction vessel, partaking in the thermocycling procure. This is however not necessarily accurate. As most plastic materials, used for reaction vessels do not absorb IR radiation, the measurement according to the present invention will actually give the temperature in the sample itself. The measurement can be governed by an algorithm, giving not only the mean temperature of the rotting vessels but also possible deviations from this mean value.

The above IR-sensor is preferably equipped with a laser, emitting a concentrated ray of light hitting the reaction vessels. This laser "point" visible on the vessels can be registered by an optional sensor and used for controlling the focus of the IR sensor, the speed of rotation, for triggering the measurement of sample temperature and for reflectometric and/or fluorometric measurements. When using the reflection of the laser to trigger the temperature measurements, a higher accuracy can be reached Further, in order to avoid interference between the IR-sensor and an IR-source, possibly used for heating the reaction vessels, the IR-source should be chosen so as to emit IR radiation at a wavelength clearly different from the reading wavelength of the IR-sensor.

The simultaneous cooling from the opposite direction of the gravitation field, provided according to one embodiment of the invention, efficiently increases the degree of density homogenisaton, that is, shortens the time for temperation and homogenisation of the reaction mixture.

A method according to the invention comprises the following steps:

i) at least one reactant is measured into a reaction vessel, ii) said reaction vessel with contents is placed in a device capable of subjecting it simultaneously to centrifugation and heating; and iii) said reaction vessel is subjected to centrifugation iv) the distal end of the reaction vessel is subjected to heating.

According to a preferred embodiment of the invention at least one reactant is added using a capillary or similar device, which only releases its content upon centrifugation.

A method according to an embodiment of the invention comprises the following steps:

i) at least one reactant is measured into a reaction vessel, said vessel carrying information regarding the intended treatment or process steps, ii) the information is read by a device, part of or connected to a device capable of subjecting it simultaneously to centrifugation and heating, iii) said reaction vessel with contents is placed in the above device for centrifugation and heating; and iv) said reaction vessel is subjected to centrifugation, v) the distal end of the reaction vessel is subjected to heating;

vi) steps iv and v being performed according to the information contained on the reaction vessel.

When performing the method according to the steps i) through vi) above, the risk of operator error is minimized if not entirely removed. The method also allows a large extent of automation of the process and further, it simplifies the compliance with quality control schemes.

In general, the present invention also discloses a new method for performing chemical reactions in fluid media contained in reaction vessels, characterized in that a device according to any one of attached apparatus claims is used.

In particular, the present invention discloses a novel and efficient method for performing reactions demanding a high degree of homogenization and involving repeated temperation e.g. analyses and synthesis involving themocycling. One example of such analyses is the polymerase chain reaction (PCR) technique. Another important application is in the field of high throughput screening. This and other methods are outlined previously in the description.

The device according to the invention is particularly suitable for a variation of the PCR analysis, generally known as "hot start PCR". Using the inventive device, the temperature is first set to a temperature above the annealing temperature of the primers. During this initial temperation, the rotor is rotated on a lower speed, sufficient to assist in temperation. When the desired temperature is reached, the reagents are added with the aid of reagent capillaries or reagent cartridges (e.g. capillaries or cartridges as disclosed in PCT/SE91/00343 and PCT/SE97/01562 by same applicant). The emptying of the regent capillaries or cartridges is triggered by increasing the speed of rotation. At a higher rotational speed, the capillaries or cartridges are emptied by the centrifugal force and the PCR analysis can be carried on, as described above in the description.

When performing a PCR-analysis using a device or apparatus according to the present invention, the time required for the amplification steps is significantly shortened. In practical experiments performed by the inventor, a PCR amplification normally requiring about 2 hours for completion, can now be performed in less than 20 minutes with unaffected or improved results. The results were confirmed on SDS-Page gels, which showed high specificity and resolution.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

What is claimed is:

1. A method for performing chemical or biochemical reactions involving temperature and homogenization, comprising the steps of:
   a) loading a reaction vessel with a reaction mixture to be homogeneously incubated,
   b) subjecting said reaction vessel and its content to a centrifugal force exceeding 500×g, and
   c) heating and/or cooling the reaction mixture in said reaction vessel under said centrifugal force, whereby the gravitation field acting upon more dense subsets of the reaction mixture leads to a thoroughly mixed homogeneous reaction mixture and a homogeneous temperature distribution in the bulk of the reaction mixture.

2. The method according to claim 1, wherein,
   the homogenization with respect to temperature in the bulk of the reaction mixture step c) is performed by simultaneous heating a first portion of the reaction mixture and cooling a second portion of the reaction mixture,
   the heating is performed using a radiation source emitting radiation within a wavelength generating heat in the reaction mixture contained in said reaction vessel and by air at a temperature of 200°C. to 800° C.

3. The method according to claim 1, wherein the centrifugal force is in the range of 500 to 20,000×g.

4. The method according to claim 1, wherein the centrifugal force is in the range of 1,500 g to 20,000×g.

5. The method according to claim 1, wherein the centrifugal force is in the range of 5,000 to 15,000×g.

6. The method according to claim 1, wherein the heating of the reaction vessel is performed using a radiation source emitting radiation within a wavelength generating heat in the reaction mixture contained in said reaction vessel.

7. The method according to claim 1, wherein the cooling of the reaction vessel is performed by rotating the reaction vessel in an environment containing one of ambient air, refrigerated air, a refrigerated gas other than air.

8. The method according to claim 1, wherein the temperature measurement is performed using an IR-sensor monitoring the temperature of the contents in the rotating vessels.

9. The method according to claim 1, wherein the temperation and homogenization involves repeated temperation in the form of cyclic temperature changes.

10. The method according to claim 1, wherein the homogenization with respect to temperature in the bulk of the reaction mixture step c) is performed by simultaneously heating a first portion of the reaction mixture and cooling a second portion of the reaction mixture.

11. The method according to claim 1, wherein the reaction is a PCR reaction.

12. The method according to claim 1, wherein said reaction mixture is heated by air, wherein said air is heated at a temperature of 200° C. to 800° C.

13. The method according to claim 1, wherein said reaction mixture is heated by air, said air at a temperature of 600° C.

14. The method according to claim 11, wherein said PCR reaction is completed in 20 minutes or less.

15. A device for performing chemical or biochemical reactions involving temperation and homogenization, comprising:
   a) means for holding a reaction vessel containing a reaction mixture to be homogeneously incubated,
   b) means for subjecting the reaction vessel and its content to a centrifugal force, and
   c) means for heating and cooling the temperature of the contents of the reaction vessel to temperatures appropriate for desired reactions under said centrifugal force, whereby the gravitation field acting upon more dense subsets of the reaction mixture leads to a thoroughly mixed homogeneous reaction mixture and a homogeneous temperature distribution in the bulk of the reaction mixture.

16. The device according to claim 15, wherein said means for subjecting the reaction vessel and its contents is capable of creating a centrifugal force that exceeds 500×g.

17. The device according to claim, 16, wherein said means for subjecting the reaction vessel and its contents is capable of creating a centrifugal force that exceeds 1,500 g to 20,000×g.

18. The device according to claim 16, wherein said means for subjecting the reaction vessel and its contents is capable of creating a centrifugal force that exceeds 5,000 to 15,000× g.

19. The device according to claim 16, wherein the means for heating the contents of the reaction vessel comprise means emitting radiation within a wavelength generating heat in the reaction mixture contained in said reaction vessel.

20. The device of claim 16, wherein the means for air to heat the reaction mixture, the air heated of 200° C. to 800° C.

21. The device according to claim 15, wherein said means for subjecting the reaction vessel and its contents is capable of creating a centrifugal force that exceeds 500 to 20,000×g.

22. The device according to claim 15, wherein the means for cooling the contents of the reaction vessel comprise means for exposing a rotating reaction vessel to an environment containing one of ambient air, refrigerated air, a refrigerated gas other than air.

23. The device according to claim 15, wherein the means for measuring the temperature of the reaction mixture comprise means for monitoring IR radiation emitted by the reaction mixture.

24. The device according to claim 15, wherein the means for heating and cooling the temperature is capable of repeated temperation in the form of cyclic temperature changes.

25. The device according to claim 15, wherein the heating and cooling means is capable of conducting simultaneous heating and cooling by heating a first portion of the contains and, at the same time, cooling a second portion of the contents.

26. The device according to claim 15, wherein the device is capable of performing a PCR reaction.

* * * * *